United States Patent [19]

Ness

[11] Patent Number: 4,880,419

[45] Date of Patent: Nov. 14, 1989

[54] ABSORBENT ARTICLE WITH INTERNAL WICKING MEANS

[75] Inventor: Irving S. Ness, Palmetto Dunes, S.C.

[73] Assignee: Chicopee, New Brunswick, N.J.

[21] Appl. No.: 284,049

[22] Filed: Dec. 14, 1988

Related U.S. Application Data

[63] Continuation of Ser. No. 152,208, Feb. 3, 1988, Pat. No. 4,842,594, which is a continuation of Ser. No. 889,448, Jul. 23, 1986, abandoned, which is a continuation of Ser. No. 721,832, Apr. 10, 1985, which is a continuation-in-part of Ser. No. 525,850, Aug. 24, 1983, abandoned.

[51] Int. Cl.⁴ .............................................. A61F 13/16
[52] U.S. Cl. ..................................... 604/368; 604/378
[58] Field of Search ............... 604/367, 368, 369, 378, 604/379, 358, 385.1, 374, 375

[56] References Cited

U.S. PATENT DOCUMENTS

| | | | |
|---|---|---|---|
| 810,135 | 1/1906 | Green | 604/378 |
| 3,375,827 | 4/1968 | Bletzinger et al. | 604/369 X |
| 3,468,311 | 9/1969 | Gallagher | 604/378 |
| 3,838,693 | 10/1974 | Sherman | 604/378 |
| 4,014,338 | 3/1977 | Schaar | 604/378 X |
| 4,232,674 | 11/1980 | Millican | 604/378 X |
| 4,251,643 | 2/1981 | Harada et al. | 604/368 X |

FOREIGN PATENT DOCUMENTS

| | | | |
|---|---|---|---|
| 1492430 | 3/1970 | Fed. Rep. of Germany | 604/378 |
| 6707397 | 12/1967 | Netherlands | 604/378 |
| 7701851 | 8/1978 | Netherlands | 604/368 |

*Primary Examiner*—John D. Yasko
*Attorney, Agent, or Firm*—Lawrence D. Schuler

[57] ABSTRACT

An absorbent article comprising at least two discrete superabsorbent containing layers and a wicking means extending about and between the superabsorbent containing layers.

13 Claims, 3 Drawing Sheets

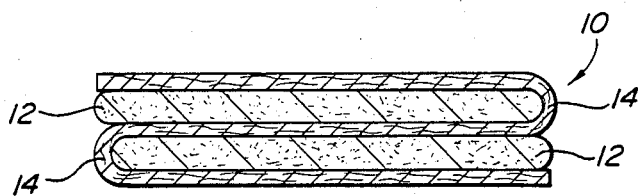
FIG-1
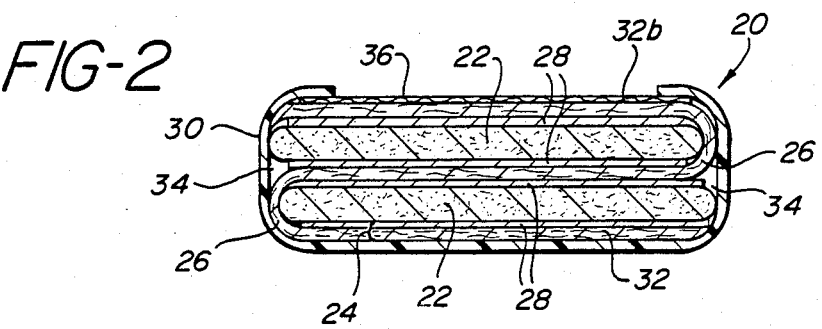
FIG-2
FIG-2A
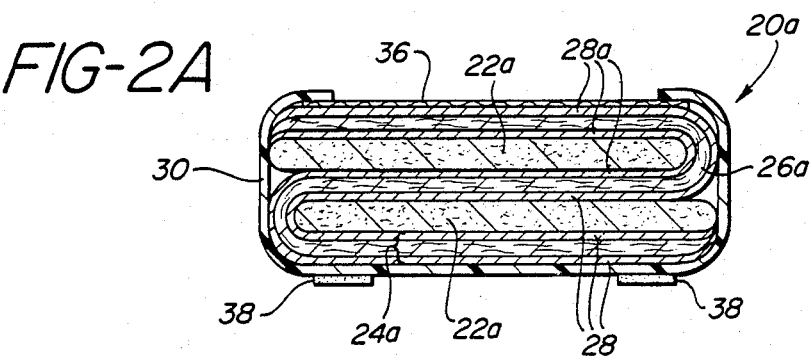
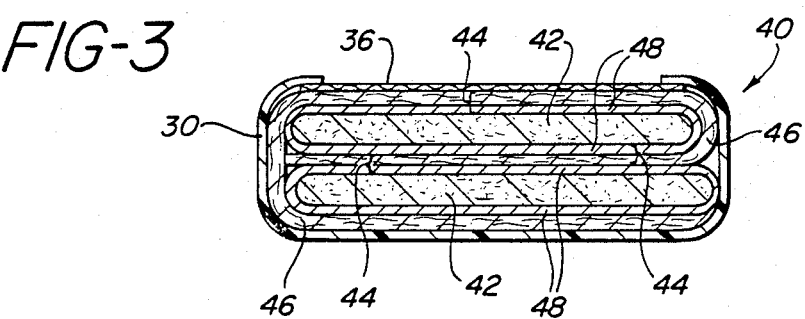
FIG-3

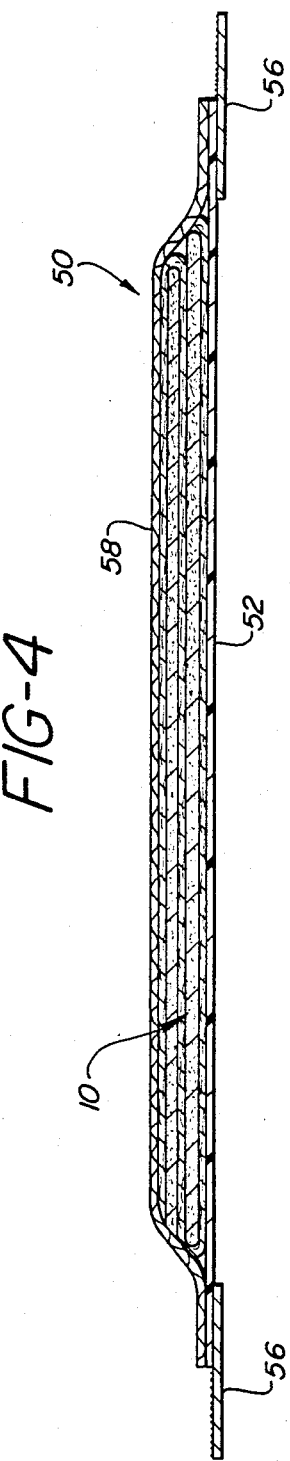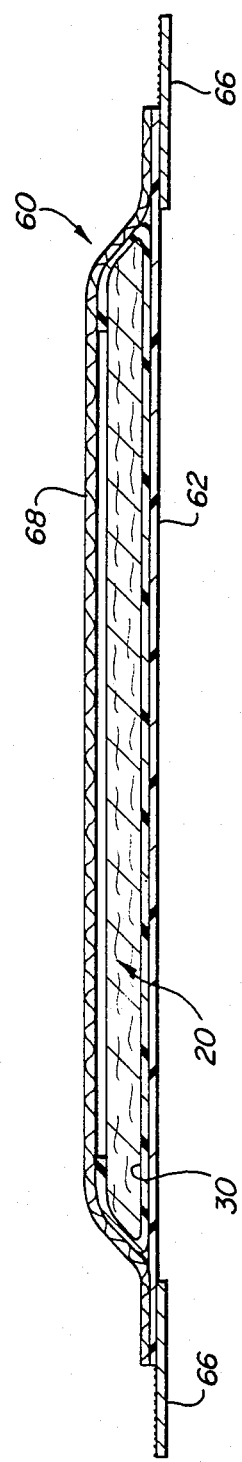

ABSORBENT ARTICLE WITH INTERNAL WICKING MEANS

This is a continuation of application Ser. No. 152,208, filed Feb. 3, 1988 now U.S. Pat. No. 4,842,594, which is a continuation of application Ser. No. 889,448, filed July 23, 1986 now abandoned, which is a continuation of application Ser. No. 721,832, filed Apr. 10, 1985, which is a continuation-in-part of application Ser. No. 525,850, filed Aug. 24, 1983 now abandoned.

BACKGROUND OF THE INVENTION

The use of superabsorbents in absorbent articles permits a substantial reduction in the bulk of the absorbent article. However, attempts to utilize superabsorbent materials in absorbent structures such as diapers and sanitary napkins have met with limited success. It is often difficult to "fix in place" or secure superabsorbents within the absorbent article. U.S. Pat. No. 3,971,379 discloses absorbent articles wherein a layer of superabsorbent is folded or rolled with another absorbent component of the absorbent article. Secondly, superabsorbent materials absorb and retain hundreds of times their weight of fluids, but they do not easily wick fluids. In an absorbent article, rapid swelling of the superabsorbent together with its lack of wicking ability can create a fluid "block", preventing the utilization of the remainder of the superabsorbent, or other absorbent materials in the absorbent article.

New methods of utilizing superabsorbents into absorbent articles focus on methods of incorporating the superabsorbent into a fibrous structure so as to avoid the blocking problem. U.S. Pat. No. 4,105,033 discloses a method of incorporating a superabsorbent into a fibrous structure, and U.S. Pat. No. 4,226,237 discloses a more elaborate fibrous structure of absorbent fibers and peat moss, into which superabsorbent may be distributed.

The present invention involves a new approach to the use of superabsorbents in an absorbent article. Rather than attempt to create new fibrous structures wherein the superabsorbent is so dispersed as to prevent blocking, the present invention may use known fibrous materials containing superabsorbents which materials when used alone may block. In the absorbent article of the present invention, the superabsorbent may be dispersed within a fibrous structure or cellular foam or may be present in a film, alone or together with other ingredients. According to the present invention, an internal wicking means is provided within the absorbent article to bring the fluid to the superabsorbent. The wicking means is wrapped or folded about discrete layers containing the superabsorbent.

Methods of folding absorbent fibrous materials to form absorbent articles are shown in U.S. Pat. No. 2,952,259. However, there is no teaching of superabsorbents or internal wicking means.

SUMMARY OF THE INVENTION

The present invention comprises an absorbent article having discrete superabsorbent containing layers. The absorbent article has a wicking means which is wound about and between the superabsorbent containing layers. The wicking means comprises a wicking layer, and a fluid transfer means between the wicking layer and the superabsorbent containing layers. The superabsorbent containing layers may comprise superabsorbent ingredients dispersed within a fibrous layer or upon a fibrous layer, or superabsorbent dispersed within a cellular foam material, or films made partially or entirely of superabsorbent materials. Acrylic fibers, peat moss, wood pulp fibers, or tissue or mixtures thereof may provide the wicking layer. The fluid transfer layer is formed of similar materials, but provides a higher capillary pressure for the liquid than that possessed by the wicking layer. A partial outer wrap of fluid impermeable material may be disposed about all but one major surface of the absorbent article. In a disposable diaper the plastic film partial outer wrap may be sealed to the outer surface of the disposable diaper, reinforcing the diaper and enhancing the repositionability of adhesive tape tabs thereto.

BRIEF DESCRIPTION OF THE DRAWINGS

FIG. 1 shows a schematic cross-section of one embodiment of the absorbent article of the present invention;

FIG. 2 shows a cross-section of one embodiment of the absorbent article shown schematically in FIG. 1;

FIG. 2A shows a cross-section of another embodiment of the absorbent article shown schematically in FIG. 1;

FIG. 3 shows a cross-section of another preferred embodiment of the absorbent article of the present invention;

FIG. 4 shows a cross-section of a disposable diaper incorporating the absorbent article of the present invention;

FIG. 5 shows a cross-section of a preferred embodiment of a disposable diaper incorporating the absorbent article of the present invention.

DETAILED DESCRIPTION OF THE INVENTION

Figure 6:
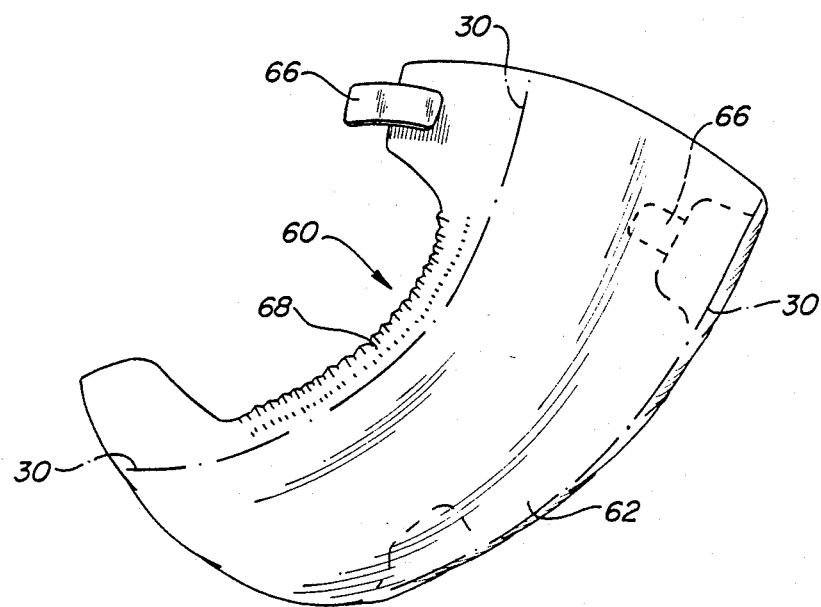
FIG. 6 shows a perspective view of the diaper of FIG. 5.

The present invention comprises an absorbent article which utilizes superabsorbent materials in a novel way. According to the present invention, an internal wicking means is utilized to move fluid within an absorbent article that contains superabsorbent materials.

As shown schematically in FIG. 1, one embodiment of the absorbent article of the present invention shown generally at 10 comprises at least two discrete layers 12 having a superabsorbent material incorporated therein. The absorbent article further comprises a wicking means 14 which extends in an S-shape wound about and between the superabsorbent layers. The present invention does not rely on the form or construction of the superabsorbent containing layer, and many varieties of materials incorporating superabsorbent agents may be utilized. For instance, the superabsorbent containing layer may comprise superabsorbent material incorporated within a fibrous layer, or a cellular foam layer. The method of incorporating the superabsorbent into the fibrous layer or cellular foam is not critical as it is not required that fluid pass through the superabsorbent containing layer, but only that the surfaces of the superabsorbent material is contacted by the liquid. Indeed, according to the present invention, the superabsorbent containing layers may comprise films made wholly or in part of superabsorbent materials. In the absorbent article of the present invention, the superabsorbent containing layers need not wick or transport fluid as the internal wick of the absorbent article brings the fluid to the superabsorbent material. Hence, when the superabsorbent material within the layers swells, it tends not to block the movement of the fluid through the absorbent article. If the superabsorbent in any particular part of the absorbent article swells or reaches saturation, the internal wicking means merely moves the fluid to be absorbed on to the next available superabsorbent material.

The following test data demonstrate the superiority of Applicant's absorbent article having internal wicking means. The absorbent capacity of three diaper structures incorporating the absorbent article of the present invention as described in FIG. 1 was tested. In the test procedure used, which is intended to simulate diaper use, the diapers are fastened around a lifesize doll and test solution is poured through the doll into the diaper in 50 milliliter aliquots, with a twenty minute wait between aliquots. The test is stopped at the first indication of a leak. The diapers are weighed before and after the test so that the amount of liquid absorbed by the diaper can be determined. Each of the diapers had a co-extruded Visqueen polypropylene film backing ($17\frac{1}{2}'' \times 12''$) and a similarly sized facing material of 100 percent embossed polypropylene 0.7 oz/yd.$^2$ fabric. The superabsorbent containing layers comprise 8 gm/ft$^2$ Henkel fabric S6P manufactured by the Henkel Corporation. The Henkel fabric comprises S6P-147, a ceric ion catalyzed starch acrylonitrile graft polymer in powder form, sandwiched between two layers of tissue. In diaper No. 1, the absorbent body of the diaper, contained between the facing and backing sheet, comprised two layers of the Henkel superabsorbent fibrous layer S6P and had no internal wick. The absorbent capacity was 72.8 grams. In diaper No. 2, the absorbent article, incorporated between the backing and the facing comprises two layers of the same Henkel fabric with an S-shaped wicking layer of tissue. The absorbent capacity of diaper No. 2 was 165.9 grams. In diaper No. 3, the absorbent article, contained between the backing sheet and the facing, comprised two layers of the same Henkel superabsorbent fibrous layer, and an S-shaped internal wicking layer of acrylic fiber fabric. The absorbent capacity of diaper No. 3 was 179.1 grams.

FIG. 2 discloses one embodiment of the absorbent article of the present invention shown schematically in FIG. 1. In this embodiment, the absorbent article shown at 20 comprises superabsorbent containing layers 22 and an internal wicking means 24 which comprises a wicking layer 26 and a fluid transfer means 28. The wicking layer 26 may comprise any material which has good wicking properties. It is not required that this material have good absorbent capacity or be able to retain fluids under stress. Suitable materials for use as the wicking layer are acrylic fibers, wood pulp fibers, tissue material, or peat moss. Fluid transfer means may be present between the wicking layer and at least the major surfaces of the superabsorbent containing layers. The fluid transfer means is any of the materials suitable for the wicking layer but the material is in a form so as to provide a higher capillary pressure in the fluid transfer means than that provided by the wicking layer. In the examples listed above, the tissue layers of the Henkel fabric serve as the fluid transfer means. The fluid transfer means 28 effects the transfer of the fluid from the wicking layer to the superabsorbent containing layer. The use of the intermediate fluid transfer means aids in keeping the internal wicking means or pathway open at all times and allows the wicking layer to wick while the fluid transfer means holds and gradually releases the fluid for absorption in the superabsorbent containing layers.

The higher capillary pressure fiber fluid transfer means provides the mechanism for draining a substantial portion of the liquid from the wicking layer and making it available to the superabsorbent material. As the superabsorbent material takes liquid from the fluid transfer means, the fluid transfer means takes liquid from the wicking layer. What appears to be only a small difference in capillary pressure, is all that is required for the fluid transfer means to attract and drain the wicking layer of liquid the latter has received. The force causing a liquid to enter a cylindrical capillary is expressed by the equation:

$$P = \frac{(2v \cos \theta)}{r}$$

wherein the force is represented by the capillary pressure and:

P is the capillary pressure,
v is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from the wider ones.

The relative wickability between the fluid transfer means and the wicking layer is affected by both the relative densities of the layers and the relative wettability of the individual fibers in each layer. The individual fibers of the fluid transfer means have substantially smaller liquid-fiber contact angles than those of the wicking layer overcoming the density difference and providing a significant overall increase in capillary pressure to absorb liquid into the fluid transfer means.

The fluid transfer means fibers and the density of the layer are selected to create the small, but significant difference in capillary pressure from the wicking layer.

The superabsorbent material used in the superabsorbent containing layer is generally a water-insoluble but water-swellable polymeric substance capable of absorbing water in an amount which is at least 10 times the weight of the substance in dry form. The superabsorbent material is in the form of particles, or fibers, or spheres, or bits of film, or globules or the like. In addition, the superabsorbent may be formed in situ by spraying a liquid monomer solution onto a fibrous web or fabric and subsequently polymerizing and cross-linking the monomers to provide the water-insoluble, water-swellable polymeric substance.

One type of suitable superabsorbent in the form of particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula:

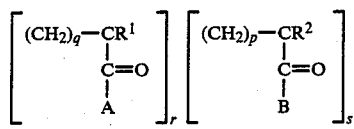

wherein A and B are selected from the group consisting of $-OR^3$, $-O$ (alkali metal), $-OHNH_3$, $-NH_2$, wherein $R^1$, $R^2$ and $R^3$ are selected from the group consisting of hydrogen and alkyl having 1 to 4 carbon atoms, wherein r is an integer having a value of 0 to about 5000 or more, s is an integer having a value of 0 to about 5000 or more, r plus s is at least 500, p is an integer having a value of zero or 1 and q is an integer having a value of 1 to 4. The preferred hydrophilic chains are hydrolyzed polyacrylonitrile chains and copolymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combinations of cations), acrylate, may be placed on the absorbing layer by spraying or otherwise placing a solution thereon followed by polymerization and cross-linking, for example, by irradiation.

Other suitable superabsorbent includes naturally occurring materials such as gums, and the like. Guar gum, acacia gum, and locust bean gum are examples of suitable gums.

The absorbent article 20 of FIG. 2 has major surfaces 32 and 32b, side edges 34, and end edges, not shown. The absorbent article may have a partial outer wrap 30 of a fluid impervious material, which covers at least one major surface 32 and the side edges 34 of the absorbent article, and may also cover the end edges. This partial outer wrap comprises a preferred construction of the absorbent article, as the fluid impermeable layer retains the fluid in the absorbent article, allowing time for the fluid to be absorbed by the superabsorbent layers. In addition, in an absorbent article utilizing this wrapped construction, the fluid impervious layer hides of the off color appearance or texture of other absorbent materials e.g., reground pulp, used in the absorbent article and encapsulates and hides the gel-like nature of the superabsorbent when wetted. This preferred absorbent article may also be provided with a facing layer 36 on the other major surface 32b not covered by the partial outer wrap.

FIG. 2A discloses another embodiment of the absorbent article of the present invention shown schematically in FIG. 1. The absorbent article shown generally at 20a comprises superabsorbent containing layers 22a and internal wicking means 24a. The wicking means comprises a wicking layer 26a and fluid transfer means 28a. As shown in this embodiment, the fluid transfer means may comprise a layer coextensive with the wicking layer. In this construction, the wicking layer may be incorporated between two layers of fluid transfer means, and this multilayer composite structure wound in an S-shape about and around the superabsorbent containing layers. This construction of the wicking means and of the absorbent article of the present invention differs from that shown in FIG. 2 wherein the fluid transfer means is disposed between the wicking layer and the major surfaces of each superabsorbent layer. This embodiment may also incorporate a fluid-impermeable layer 30 and a facing layer 36 comparable to those described at 30 and 36 of FIG. 2. When used as a sanitary napkin the absorbent article may further comprise adhesive strips 38 for attachment to an undergarment.

FIG. 3 shows another embodiment of the absorbent article of the present invention, shown generally at 40. The absorbent article shown here in cross-section comprises superabsorbent containing layers 42 and an internal wicking means 44 which comprises a wicking layer 46 wound about and between the superabsorbent containing layers in an "e" shape. The wicking means comprises a wicking layer 46 and a fluid transfer means 48. In the particular embodiment shown, each of the superabsorbent containing layers has been wrapped in a fluid transfer means such as tissue prior to the winding of the wicking layer about and between the superabsorbent containing layers. When the wrapping of the fluid transfer means and the winding of the wick is completed, the wicking layer extends across the major surfaces of the superabsorbent containing layers and fluid transfer means are disposed between the wicking layer and each major face of the superabsorbent containing layers. The juxtapositioning of the wicking layer and fluid transfer means to this superabsorbent containing layer provides an internal wicking means for the superabsorbent containing layers. Optionally, this embodiment of the absorbent article of the present invention may also incorporate a facing layer 36 and a partial outer wrap 34 as described in relation to FIGS. 2 and 2A.

The superabsorbent materials utilized in the present invention comprise various hydrocolloid and hydrogel materials as hereinbefore described which have the ability to absorb 10 to 30 times their own dry weight and preferably many hundreds of times their own dry weight of fluids. Many superabsorbent materials are known in the art and the present invention does not depend on the chemical or physical structure of the superabsorbent, or the structure of a composite wherein the superabsorbent is incorporated with other materials, e.g., fibers in a fibrous layer. Because the absorbent article of the present invention comprises discrete superabsorbent layers, it avoids the "working" by folding and bending of the fibrous layer or cellular foam layer which may cause the superabsorbent to become disattached from the fibrous layer or cellular foam, and agglomerate. In addition, the construction of the absorbent article of the present invention provides an easier method of manufacture than folding of the superabsorbent containing layers and requires a lesser length of wicking material in the wicking layer than would be utilized in a folded shape such as that shown in U.S. Pat. No. 3,791,379.

FIG. 4 discloses a disposable diaper utilizing the absorbent article of the present invention. The absorbent article of the present invention may be utilized in many structures such as sanitary napkins and dressings, as well as in various diaper structures. FIG. 4 discloses a diaper structure shown generally at 50, said structure comprising an outer layer 52, an absorbent article of the present invention 10, attached thereto, and tape tabs 56. The diaper may further comprise a facing layer 58 comprising the inside surface of the diaper.

As shown in FIG. 5, when the absorbent article of the present invention comprises a partial outer wrap 30 of fluid impermeable material as shown with relation to absorbent articles 20 (or 40, not shown) in FIGS. 2, 2A (or 3) above, it is not necessary that the outer layer 62 of the diaper, shown generally at 60, be fluid impermeable. In a preferred construction, both the outer layer 62 and the outer wrap 30 of the absorbent article comprise plastic films. The securing of the absorbent article within the diaper secures the two plastic films, reinforcing the outer layer of the diaper. As the tape tabs 66 can be more easily peeled from the two layer plastic laminate, the diaper may be opened without tearing the plastic film outer layer which can render the adhesive tape tab unusable as well as allowing the inner absorbent material of the diaper to leak out. In addition, the cleanly peeled adhesive tape tab is available to make a new diaper fastening. Also with this absorbent article construction of the present invention having an outer wrap 30, neither pulp nor superabsorbent gel may leak from the diaper.

FIG. 6 shows the diaper of FIG. 5 view from the outer surface of the diaper illustrating that the region wherein the outer layer 62 is juxaposed to the partial outer wrap 30, reinforcing the outer layer and enhancing the repositionability of the tape tabs, 66. In the preferred embodiment shown, the diaper includes elastic gathering means, in the leg regions. The facing 68 is a liquid permeable nonwoven such as polyester and is laminated to the backing or outer layer 62 around the edges of the product.

The foregoing description and drawings are illustrative but are not to be taken as limiting. Other variations and modifications are possible without departing from the spirit and scope of the present invention.

I claim:

1. An absorbent article comprising at least two discrete superabsorbent containing layers and a continuous wicking means extending about and between the superabsorbent containing layers.

2. An absorbent article as in claim 1 wherein said wicking means comprises a wicking layer and a fluid transfer means between the wicking layer and each discrete superabsorbent containing layer, said fluid transfer means being adapted to drain liquid from the wicking layer and make it available to the superabsorbent material in the superabsorbent containing layer.

3. An absorbent article as in claim 2 wherein said wicking means comprises a fluid transfer means having a higher capillary pressure than the wicking layer.

4. An absorbent article as in claim 1 wherein said superabsorbent containing layers comprise a superabsorbent material dispersed within a fibrous layer.

5. An absorbent article as in claim 1 wherein said superabsorbent containing layers comprise a superabsorbent material dispersed within a cellular foam material.

6. An absorbent article as in claim 1 wherein said superabsorbent containing layers comprise a film comprising superabsorbent material.

7. An absorbent article as in claim 1 wherein said wicking layer comprises an acrylic fiber fabric, wood pulp fibers, peat moss, or tissue material.

8. An absorbent article as in claim 1 wherein said fluid transfer means comprises tissue material.

9. An absorbent article as in claim 1 further comprising a partial outer wrap of fluid impermeable material.

10. A disposable diaper comprising a backing sheet, at least two adhesive tape tabs affixed to said backing sheet, and the absorbent article of claim 1 affixed to said backing sheet.

11. An absorbent article as in claim 1 wherein said superabsorbent containing layers comprise a superabsorbent material dispersed upon a fibrous layer.

12. An absorbent article according to claim 2 wherein said fluid transfer means comprises a layer coextensive with said wicking layer.

13. An absorbent article according to claim 2 wherein said wicking means comprises a wicking layer incorporated between two layers of fluid transfer means.

* * * * *